United States Patent [19]
Jacobs et al.

[11] Patent Number: 5,762,192
[45] Date of Patent: *Jun. 9, 1998

[54] PACKAGING CURABLE MATERIALS

[75] Inventors: Dwight W. Jacobs, River Falls, Wis.;
Kenneth E. Hoevel, Monrovia; Bruce E. Chester, Irvine, both of Calif.

[73] Assignee: Minnesota Mining and Manufacturing Company, Saint Paul, Minn.

[*] Notice: The term of this patent shall not extend beyond the expiration date of Pat. No. 5,978,007.

[21] Appl. No.: 478,602

[22] Filed: Jun. 7, 1995

Related U.S. Application Data

[63] Continuation of Ser. No. 306,446, Sep. 19, 1994, Pat. No. 5,636,736, which is a continuation-in-part of Ser. No. 350,609, May 10, 1989, Pat. No. 4,978,007.

[51] Int. Cl.$^6$ ................................................ B65D 83/10
[52] U.S. Cl. .......................... 206/369; 206/368; 206/562; 206/564; 206/63.5
[58] Field of Search ................... 206/524.4, 524.6, 206/369, 368, 562, 564, 63.5, 813, 800, 460, 485, 447; 433/9

[56] References Cited

U.S. PATENT DOCUMENTS

| | | | |
|---|---|---|---|
| 3,697,223 | 10/1972 | Kovalcik et al. | 206/524.6 X |
| 4,204,325 | 5/1980 | Kaelble | 433/9 |
| 4,581,267 | 4/1986 | Miller . | |
| 4,701,965 | 10/1987 | Landis . | |
| 4,735,318 | 4/1988 | Keffeler | 206/532 |
| 4,749,352 | 6/1988 | Nicholson | 433/9 |
| 4,822,280 | 4/1989 | Rider | 433/229 |
| 4,898,276 | 2/1990 | Georgakis | 206/369 |
| 4,978,007 | 12/1990 | Jacobs et al. . | |
| 5,348,154 | 9/1994 | Jacobs et al. . | |

FOREIGN PATENT DOCUMENTS

| | | |
|---|---|---|
| 0 316 086 | 5/1989 | European Pat. Off. . |
| 0 389 226 | 9/1990 | European Pat. Off. . |
| 0 452 492 | 5/1991 | European Pat. Off. . |

OTHER PUBLICATIONS

International Search Report.

*Primary Examiner*—Ted Kavanaugh
*Attorney, Agent, or Firm*—Jacobson, Price, Holman & Stern, PLLC

[57] ABSTRACT

Disclosed is a packaged element containing a) a substrate that transmits less than about 0.5% of actinic radiation and has at least one recess, b) a cover that transmits less than about 0.5% of actinic radiation and transmits at least part of the visible light spectrum, c) a structure for maintaining the cover in contact with the substrate such that the cover filters incident radiation entering the recess, and d) an element located in the recess and having a substance thereon that is curable by exposure to the actinic radiation. Also disclosed is an article containing a) a substrate having at least one recess with an interior surface, b) an element having a tacky substance on a surface thereof, and c) a structure for positioning the element inside the recess such that the tacky substance does not separate from the element upon removal from the recess.

18 Claims, 7 Drawing Sheets

PATIENT'S RIGHT    PATIENT'S LEFT

FIG. 10
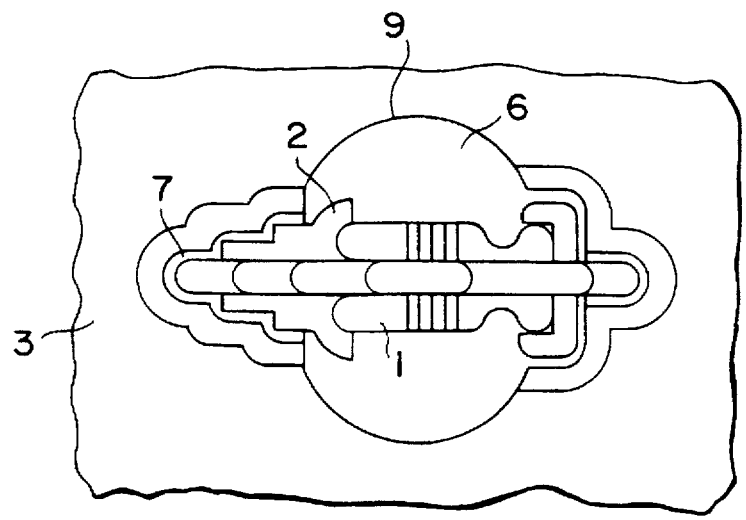
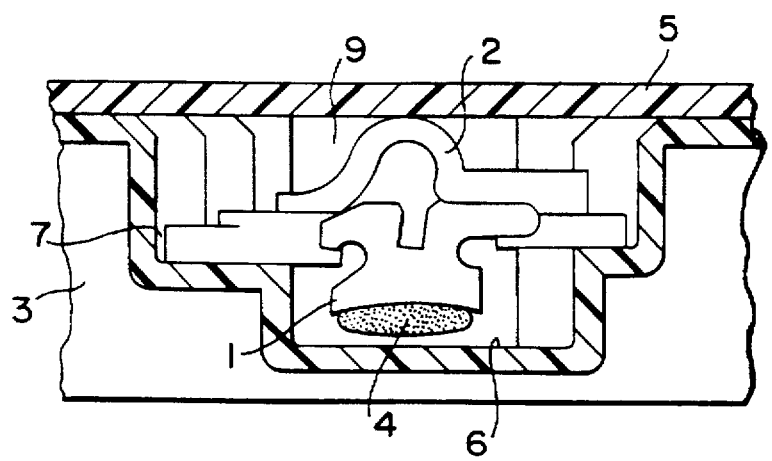
FIG. 11

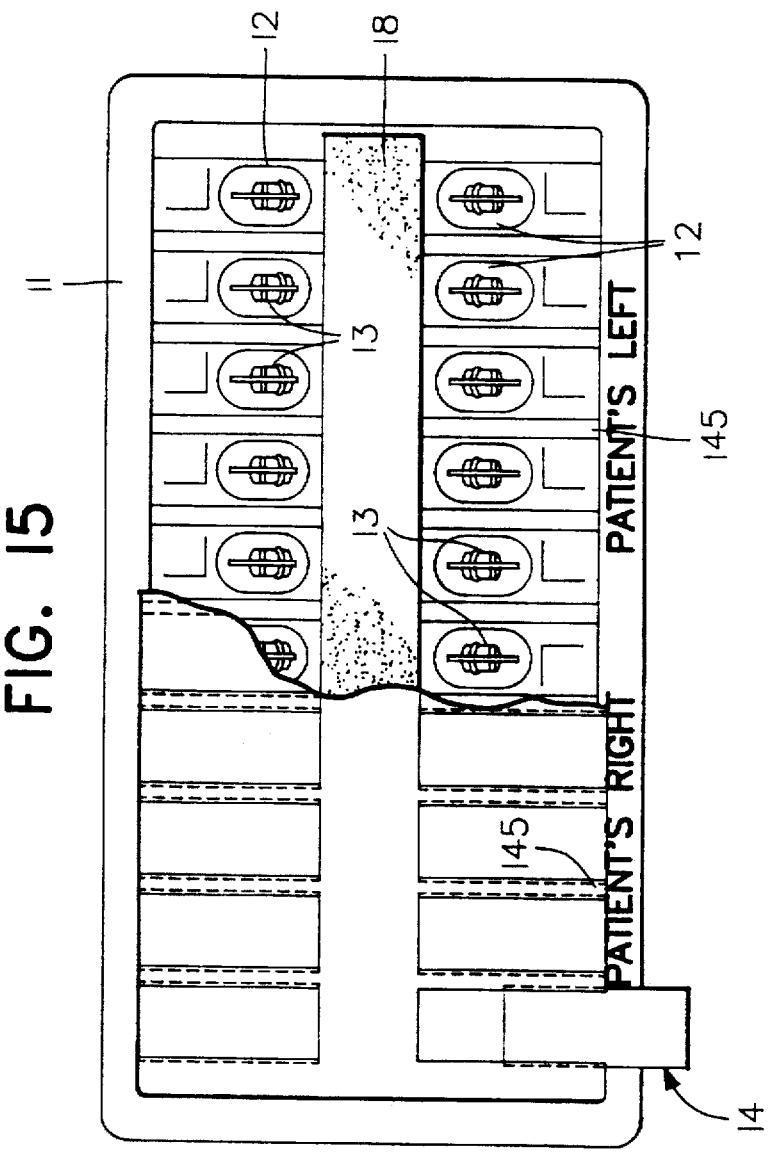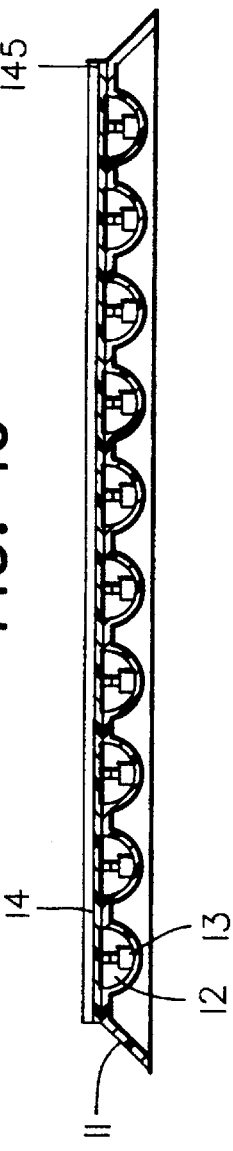

PACKAGING CURABLE MATERIALS

This application is a continuation of U.S. Ser. No. 08/306,446, filed Sep. 19, 1994, now U.S. Pat. No. 5,636,736, which is a continuation in part of U.S. Ser. No. 07/350,609, filed May 10, 1989, now U.S. Pat. No. 4,978,007, the disclosure of which is incorporated herein by reference.

This application is a continuation-in-part of U.S. patent application Ser. No. 07/350,609, filed May 10, 1989, the disclosure of which is incorporated herein by reference.

The present invention relates to packaging an element having a curable material coated thereon. In particular it relates to such a packaging wherein the materials are light-reactive, tacky, or both, and the element is an orthodontic or dental appliance. For example, such elements include dental brackets, buccal tubes, buttons, cleats, bondable retainers, and other orthodontic or dental appliances which are known to the skilled artisan.

Preferably, the element is an orthodontic bracket. Orthodontic brackets are typically packaged in bulk or in single-patient trays. Orthodontic brackets having a layer of unactivated adhesive material covered with a protective liner are disclosed in U.S. Pat. No. 4,205,325.

SUMMARY OF THE INVENTION

The present invention provides a packaged element comprising a) a substrate that transmits less than about 0.5% of selective actinic radiation and has at least one recess, b) a cover that transmits less than about 0.5% of actinic radiation and transmits at least part of the visible light spectrum, c) a means for maintaining the cover in contact with the substrate such that the cover filters incident radiation entering the recess, and d) an element located in the recess and having a substance thereon that is curable by exposure to the actinic radiation. The present invention also provides an article comprising a) a substrate having at least one recess with an interior surface, b) an element having an tacky substance thereon, and c) a means for positioning the element inside the recess such that the tacky substance does not separate from the element upon removal from the recess.

BRIEF DESCRIPTION OF THE DRAWINGS

FIG. 10 is a top view and FIG. 11 is a cross-sectional view of another preferred embodiment of the present invention. FIG. 15 is another preferred embodiment of the present invention. FIG. 16 is a horizontal sectional view of FIG. 15.

DESCRIPTION OF THE PREFERRED EMBODIMENTS

Figure 7:
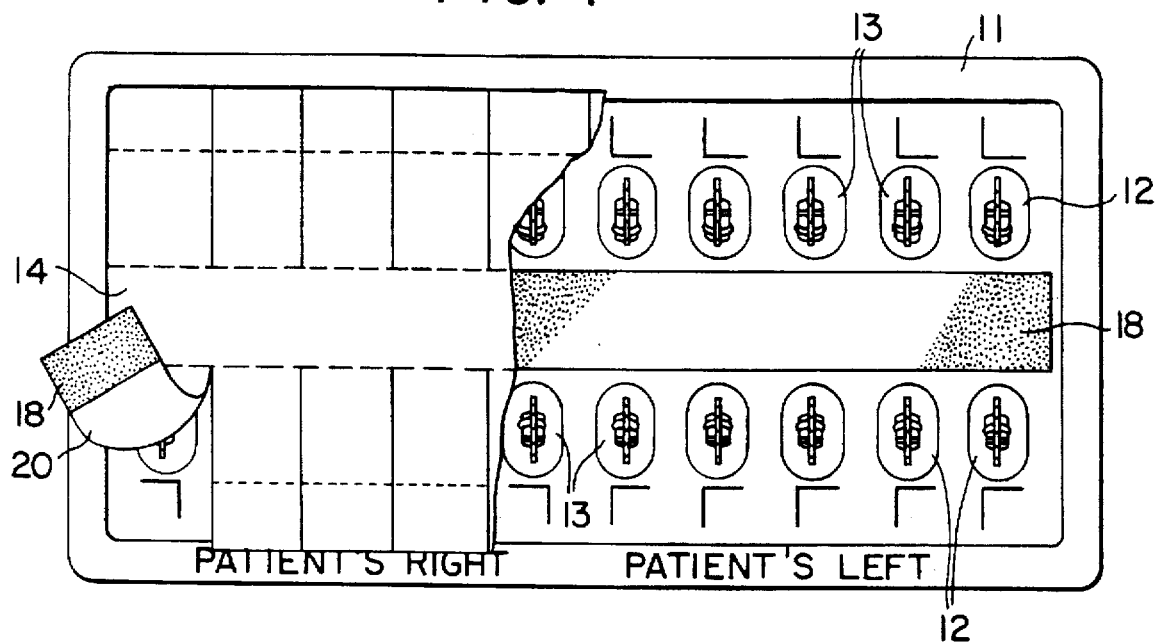
FIG. 7 is a top view.
Figure 8:
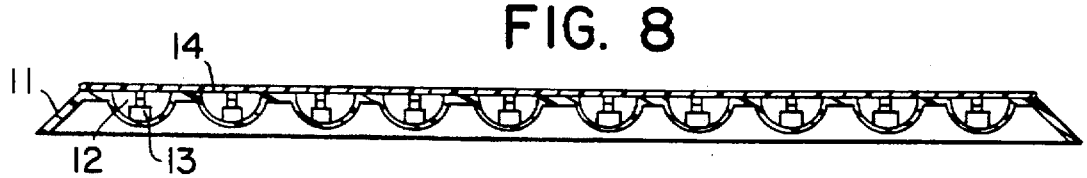
FIG. 8 is a horizontal sectional view of FIG. 7
Figure 9:
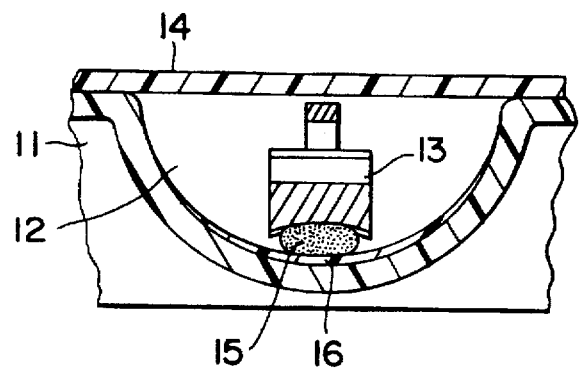
FIG. 9 is an enlarged fragmentary view of one well of a preferred embodiment of the present invention.

In one embodiment of the present invention, a tray containing orthodontic brackets pre-coated with adhesive paste and placed into release-layer-coated recesses (wells) is provided. The adhesive paste is curable upon exposure to selective actinic radiation, i.e., wavelengths of light (electromagnetic radiation) that effect curing in a particular material. Referring to FIGS. 7, 8, and 9, the embodiment contains a tray 11, such as a vacuum-formed 6.35×15.24 cm tray made from a black (opaque) semi-rigid 0.508–0.635 mm thick high-impact polystyrene sheet. The tray includes wells 12, each of which has a concave inner surface deep enough to accommodate a standard orthodontic bracket 13, which is coated with a light-curable adhesive paste 15, completely below the rim of the well. The bottom of each well is coated with an excess (0.3–0.4 grams) of a non-adhesive release-coating material 16, e.g., a silicone, polyethylene, or fluoropolymer coating such as those commercially available under the names Teflon® poly tetrafluoroethylene and Teflon® fluorinated ethylenepropylene (available from E.I. du Pont de Nemours, Wilmington, Del.) and Silicone Premium (a siloxane available from General Electric Company, Waterford, N.Y.). A blue-light-filtering film 14 covers the wells and is secured to the tray with double-sided, repositionable pressure-sensitive adhesive tape 18. The cover 14 is cut to form individual flaps 20, which allow access to individual wells as shown in FIG. 7. Each flap 20 has a piece of double-sided, repositionable pressure-sensitive adhesive tape 18, which maintains the flap in contact with the tray. Alternatively, access to the brackets can be provided by a star-burst pattern of slits cut into the film above each well. Preferably, the film is a flexible, colored transparent film, opaque to the wavelength of light required to cure the paste, but sufficiently transparent to non-curing wavelengths to permit viewing the bracket through the film.

In another embodiment of the present invention, orthodontic or dental appliances coated with a light-curable adhesive paste are provided in a tray in which each bracket is suspended in a recess designed to keep the adhesive paste from contacting the surface of the recess. As shown in FIGS. 10 and 11, bracket 1 is attached to a conventional long-axis indicator 2, the ends of which, by virtue of cooperation with complimentally-shaped, linearly-aligned grooves 7 on opposing sides of well 9 in tray 3, suspend the bracket above the bottom 6 of well 9 such that adhesive paste 4 on bracket 1 does not contact any part of the tray. Cover film 5 (not seen in FIG. 10) is attached to the tray 3 by a double-sided, repositionable pressure-sensitive adhesive tape (not shown) sandwiched between the film and the tray. As demonstrated in the figures, groove 7 and long-axis indicator 2 are shaped to engage in such a way that the indicator rests loosely in the groove while preventing lateral or rotational movement of the bracket 1 within the well 9. Cover film 5 contacts the top of the long-axis indicator 2 to hold the indicator in the groove 7. In this manner, cover film 5 and groove 7 cooperate with the long-axis indicator 2 to fix the bracket 1 loosely in the well 9.

Figure 12:
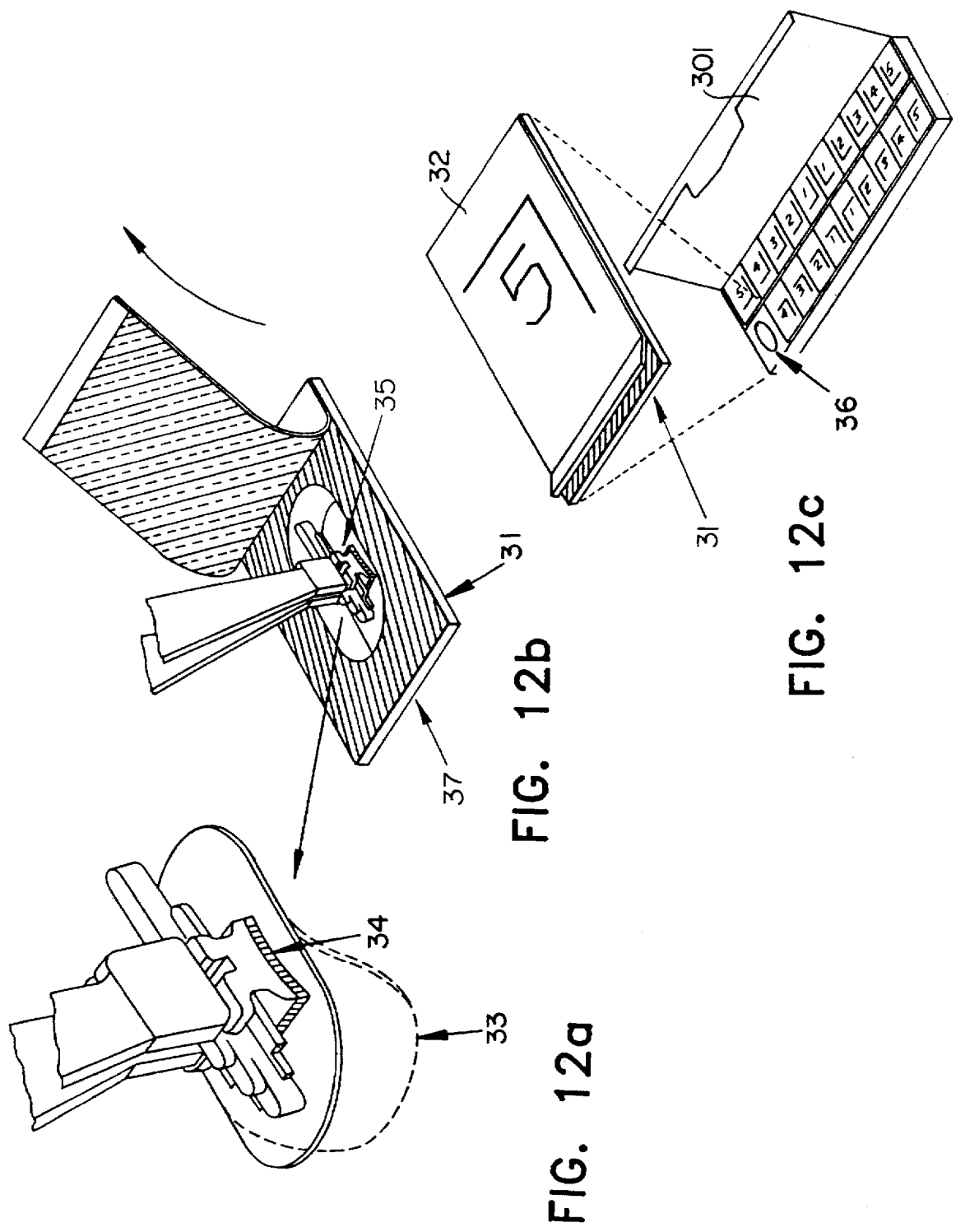
FIG. 12l–12c is another preferred embodiment of the present invention showing a removable substrate.

FIGS. 12a–12c illustrate yet another embodiment of the present invention. In this embodiment, the substrate 31, having recess 35, is provided in separate sections 37 which can be removably placed by cooperation with hole 36, into tray 30, which includes cover 30. A lid 32 is provided for each substrate section. The lid can be resealably attached to the substrate as a resealable lid, or the lid may be permanently hinged to the substrate. The lid may be opaque such that any incidental radiation is inhibited from entering the recess area of the substrate, or the lid may be such that less than about 0.5% of the actinic radiation of the visible light spectrum is transmitted.

To facilitate removal of the orthodontic bracket from the substrate, a separate release liner 33 is also provided. The release liner can be made of a material such as silicone, polyethylene, or a fluoropolymer such as those commercially available under the names Teflon® polytetrafluoroethylene and Teflon® fluorinated ethylenepropylene (available from E.I. du Pont de Nemours, Wilmington, Del.) and Silicone Premium (a siloxane available from General Electric Company, Waterford, N.Y.). The liner facilitates removal from the adhesive paste 34.

Figure 13:
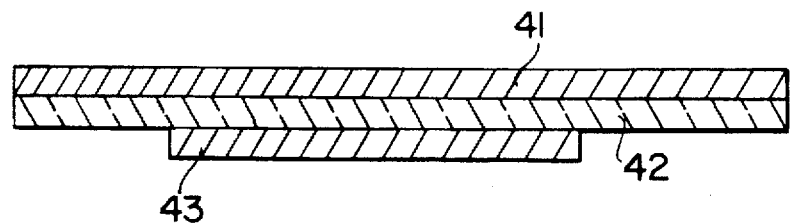
FIG. 13 shows a releasable lidding from the substrate.
Figure 14:
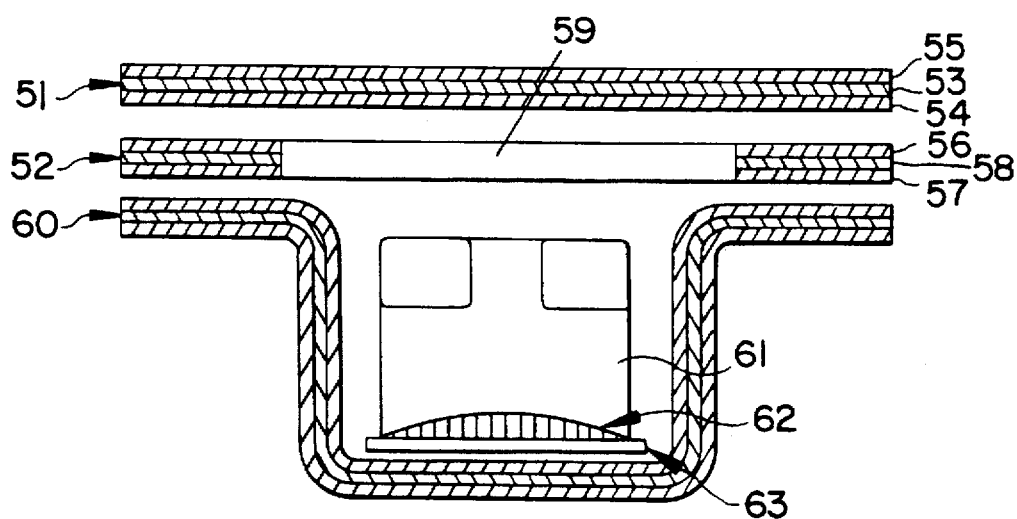
FIG. 14 shows a sectional view of the substrate and repositionable cover.

A preferred embodiment of the cover of this invention is shown in FIGS. 13 and 14. FIG. 13 details a cover having a lidding 41 attached to an inner cover material 43 by a repositionable adhesive 42. The lidding 41 is preferably a water-vapor, light, or oxygen barrier and is top coated with a printable material such that the cover can be easily labelled and identified. A plastic material such as a polyester film is preferred to be used as the water-vapor, light, or oxygen barrier. More particularly, a Mylar® film can be used as the inner cover material as well as for the lidding. By metalizing the surface of the lidding, a light barrier can be formed.

FIG. 14 illustrates a cover having a lidding 51 and adhesive 52. Preferably, the lidding includes a water-vapor, light, or oxygen barrier 53, a coating 54 for protecting the water-vapor, light, or oxygen barrier 53, and a printable top coat 55. A plastic material such as a polyester film is preferred to be used as the water-vapor, light, or oxygen barrier. More particularly, a Mylar® film can be used as the water-vapor or oxygen barrier. By metalizing the surface of the polyester or Mylar® lidding, a light barrier can be formed. The coating 54 further serves to protect the metalized surface.

The adhesive 52 of FIG. 14 preferably includes a high tack side 56 for contacting the lidding and a low tack side 57 for contacting the substrate. The high tack side can include any non-repositionable adhesive material known to the skilled artisan, and the low tack side can include any pressure-sensitive, repositionable adhesive material. A carrier 58, preferably a plastic carrier such as polyester, can be used to facilitate mounting of the adhesive layer. The cover adhesive can also include a die cut region 59 to prevent the orthodontic or dental appliance from sticking to the cover.

Also shown in FIG. 14 is a section view of the removable substrate. Shown in the substrate is the orthodontic or dental appliance 61, the light-sensitive adhesive paste 62, and the release coating 63. Preferably, the substrate is a water-vapor, light, or oxygen barrier to protect the light-sensitive adhesive paste 62.

The substrate 60 in FIG. 14 is preferably constructed of a polyethyleneterepthalate-glycol (PETG)/polyethylene/polychlorotrifluoroethylene (PCTFE) plastic. The substrate can be formed by heat and vacuum or pressure. It is preferred that the PETG layer be black to form the light barrier. However, the substrate can also be made of a material that transmits less than about 0.5% of selective actinic radiation. Although the PCTFE serves as a water-vapor and oxygen barrier, other materials known to the skilled artisan can be used. Particularly, fluorohalocarbon films such as Aclar® are desired.

Figure 1:
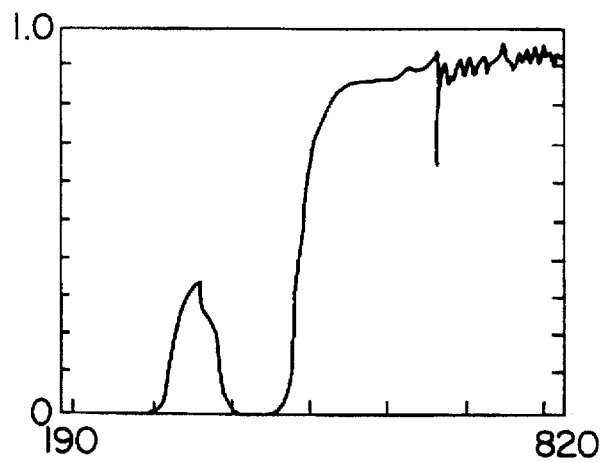
FIGS. 1–6 are curves showing % transmittance vs. wavelength (determined using a Hewlett-Packard HP 8451A Diode Array Spectrophotometer) for various dyes useful in accordance with the present invention.
Figure 4:
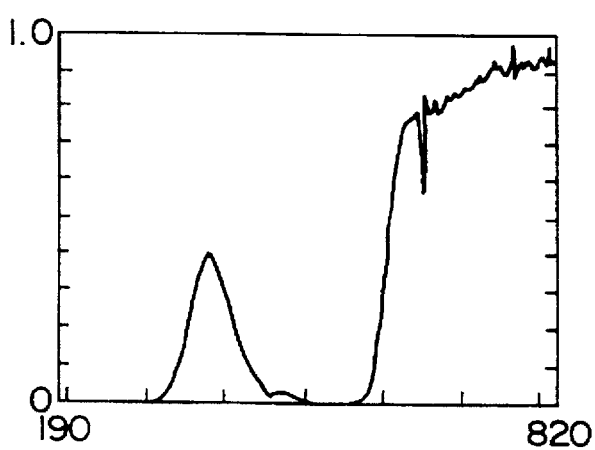
Figure 2:
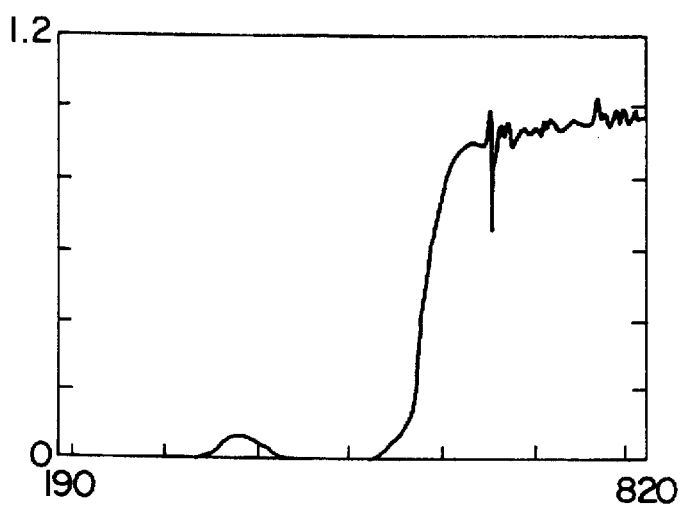
Figure 3:
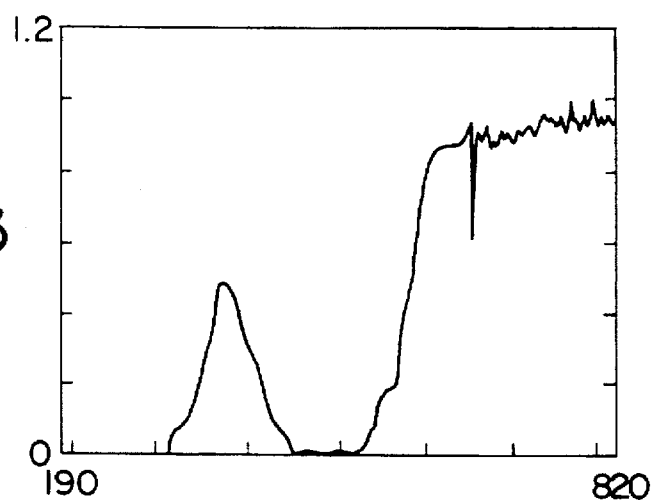
Figure 5:
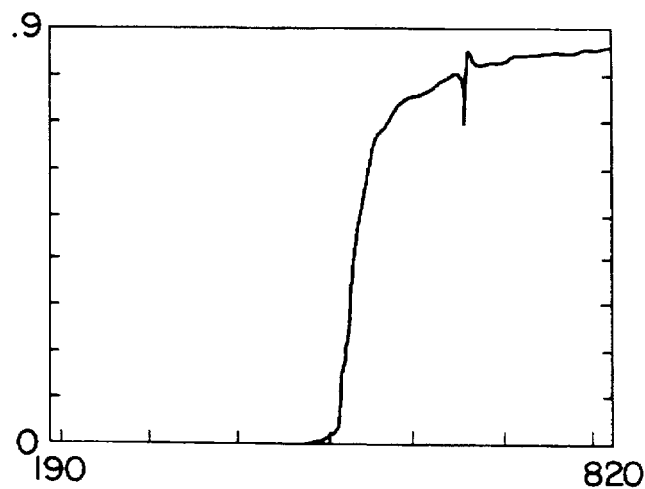
Figure 6:
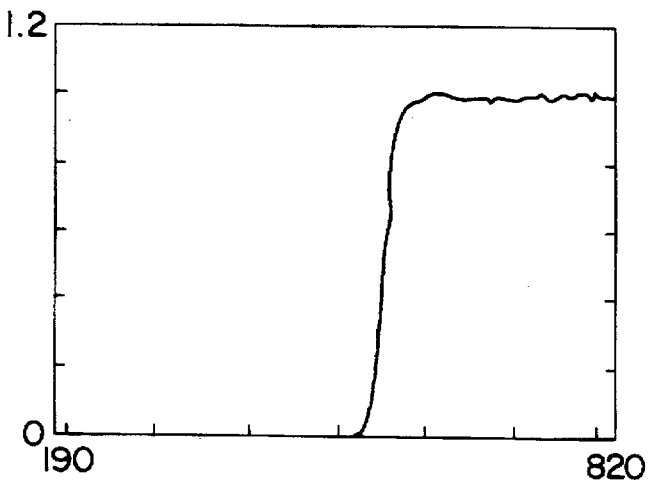

In accordance with the present invention various materials are useful for the cover and substrate. Commercially available flexible films that are useful as the cover in accordance with the present invention include, e.g., polyester materials available from Rosco Labs, Inc., Port Chester, N.Y. under the name Roscolux® 12 (38.1 µm thick, straw color, % transmittance curve for electromagnetic radiation shown in FIG. 1), Roscolux® 22 (99 µm thick, deep-amber color, % transmittance curves for electromagnetic radiation shown in FIG. 2), Roscolux® 23 (38.1 µm thick, orange color, % transmittance curves for electromagnetic radiation shown in FIG. 3), Roscolux® 42 (38.1 µm thick, deep-salmon color, % transmittance curves for electromagnetic radiation shown in FIG. 4), and vinyl materials, such as a 0.343 mm thick film having % transmittance curves for electromagnetic radiation as shown in FIG. 5 (available from Frommelt Industries, Inc. Dubuque, Iowa, under the designation Saf-T-Vu yellow, M1063). Flexible films useful as covers in accordance with the present invention have a preferable thickness between about 0.00254 and 2.54 mm, more preferably between about 0.0254 and 0.254 mm. Alternatively, rigid sheets instead of flexible films can be used, which are attached to the tray so as to permit access to the individual brackets, e.g., such as by a hinge or by cooperating tongue-and-groove appendages that permit the plate to slide relative to the tray. Useful rigid sheets include, e.g., a poly(methyl methacrylate) acrylic material having % transmittance curves as shown in FIG. 6, which has a thickness of about 3.05 mm (available from Rohm & Haas, Philadelphia, Pa. under the designation Amber 2422). Other useful covers include polymeric materials, e.g., polyesters such as poly (cyclohexane-1,4-dimethylene terephthalate), poly(ethylene terephthalate), and poly(butylene terephthalate), polycarbonates such as poly(4,4'-isopropyl-diphenyl carbonate), poly(vinyl chloride), and polypropylene. Useful rigid materials include, e.g., poly(methyl methacrylate), polyethylene, and polystyrene. Other useful cover materials include acrylic polymers, polycarbonates, polyolefins, fluorocarbon polymers, and inorganic glasses.

Various colorants (i.e., pigments, and/or dyes) are useful for making the cover absorb selective wavelengths of electromagnetic radiation. Colorants can be incorporated into both rigid sheets and flexible films according to well known methods, e.g., as disclosed in the *Modern Plastics Encyclopedia* Vol. 65, No. 11, pp. 148–150, McGraw-Hill, New York (1988). Generally, this involves blending the colorant with a molten resin and then forming the product into pellets. These pellets are then used as feed, e.g., in extruding films of desired thicknesses. The amount of colorant necessary per unit of resin to provide the desired protection will vary depending upon various factors, such as the particular colorant used, thickness of the resulting film or sheet, wavelength of light to be absorbed, and the capacity of the non-colorant-treated material to absorb light of the wavelength to be filtered. Preferably, the amount of colorant used is sufficient to enable the cover to absorb at least about 80%, preferably about 95–100%, of selective actinic radiation, i.e., light in the wavelength range useful in curing the packaged material. Alternatively, the colorant can be coated onto the cover after it has been formed. The particular colorant necessary to absorb actinic radiation from a selected range of the electromagnetic spectrum can be readily determined by the skilled artisan. Various commercially available colorants known by their color index (C.I.) identification (See *Colour Index Third Edition*, The Society of Dyers and Colourists, England, 1971) absorb (i.e., do not freely transmit) different wavelengths of the electromagnetic spectrum. For example, C.I. Disperse Yellow 201 (available from Mobay Corporation, New Jersey under the name Macrolex Yellow 6G), a styryl dye that absorbs wavelengths between about 415 and 480 nm; C.I. Solvent Blue 97 (available from Mobay Corporation under the name Macrolex Blue RR), an anthraquinone dye that absorbs wavelengths between about 550 and 650 nm; C.I. Solvent Red 135 (available from Mobay Corporation under the name Macrolex Red EC), a perinone dye that absorbs wavelengths between about 440 and 570 nm; C.I. Solvent Orange 60

(available from Mobay Corporation under the name Macrolex orange 3G), a perinone dye that absorbs wavelengths between about 380 and 515 nm; and C.I. Solvent Yellow 14 (available from Mobay Corporation under the name Ceres Orange RA), a monoazo dye that absorbs wavelengths between about 350 and 530 nm. Dyes that absorb wavelengths in the ultraviolet range (i.e., about 300–390 nm), but which impart very little color, e.g., hydroxyphenyl benzotriazoles, such as 2-(2'-hydroxy-5'-methylphenyl) benzotriazole and 2-(3',5'-di-tert-butyl-2'-hydroxyphenyl)-5-chlorobenzotriazole, and benzophenones, such as 2,4-dihydroxybenzophenone, 2-hydroxy-4-methoxybenzophenone, and 2,2'-dihydroxy-4,4'-dimethoxybenzophenone, are also commercially available, e.g., dyes available from Ciba-Geigy Corporation, New York, under the names Tinuvin®- P, -324, -326, -327, and -328 and dyes available from BASF Wyandotte Corporation, New Jersey, under the names Uvinul®-400, M-40, and D-49. The cover preferably transmits visible light outside the range of the actinic radiation that will cure the light-curable material. This allows the practitioner to see the material-coated element through the cover while retaining the light-curable material in an un-cured state. However, the cover can be opaque as well.

Various substrate materials useful in accordance with the present invention include, e.g., plastics such as poly (acrylonitrile-butadiene-styrene) copolymers (ABS polymers), poly(vinyl chloride) (PVC), poly(methyl methacrylate) (PMMA), polyethylene (PE), polystyrene (PS), and polypropylene (PP); metals, e.g., carbon steel, 303 stainless steel, and 316 stainless steel; wood, e.g., oak, maple, pine, and walnut; and other desireable materials such as ceramics and glasses. In one embodiment, the substrate is an injection-molded, black polypropylene tray. Substrates made from transparent materials, such as many plastics and glasses, are preferably opacified, using pigments such as titanium dioxide and carbon black, or modified with colorants as previously detailed for use in the cover sheet, in order to prevent electromagnetic radiation from reaching the adhesive material packaged therein. The substrate can be designed in various ways in accordance with the present invention, e.g., as shown in the accompanying figures. Other substrate examples based on the specific embodiments presented include, e.g., providing recesses large enough to accommodate more than one element, modifying the contour of the interior surface of the recesses to accommodate different shaped elements, and having projections emanating from the interior surface of the recess from which an article can be suspended. Substrates useful in accordance with the present invention can be made according to known methods, e.g., as disclosed in the aforesaid *Modern Plastics Encyclopedia*.

Various means are useful for maintaining the cover in contact with the substrate in accordance with the present invention. Preferably, an adhesive is used, either by itself or as part of a double-sided or single-sided adhesive tape. The adhesive can be an aggressive (permanent) adhesive, e.g., as disclosed in U.S. Pat. Nos. 3,691,140, 3,873,638, 3,922,464, 4,379,883, 4,413,080, 4,599,265, or RE 24906, the disclosures of which are incorporated herein by reference. Alternatively, the adhesive can be a pressure-sensitive, repositionable adhesive, e.g., as disclosed in U.S. Pat. Nos. 3,620,988, 3,691,140, 3,857,731, 4,166,152, 4,587,152, 4,645,783, 4,656,218, 4,735,837, and 4,786,696, the disclosures of which are incorporated herein by reference. In addition to adhesive means, other useful means include a hinge-and-clasp fastening arrangement, which permits lifting of the cover to permit removal of a bracket and then lowering and fastening the cover to the substrate to protect the remaining brackets, or a tongue-and-groove arrangement, which permits sliding of the cover with respect to the substrate. The cover can also be heat-sealed to the substrate. Additionally, the cover can be in one piece covering all of the recesses in the substrate, or in several pieces, either completely separate or partially connected, each piece covering one or more substrate recesses.

The present invention is useful for packaging a variety of elements in accordance with the present invention, e.g., adhesive-coated orthodontic brackets as discussed above. Useful adhesive-coated orthodontic brackets include, e.g., those disclosed in U.S. Pat. No. 4,204,325 and European Pat. Application No. 0 290 133, the disclosures of which are incorporated herein by reference. Other useful elements containing radiation-curable materials, tacky materials, or both will be apparent to the skilled artisan.

What is claimed is:

1. An assembly comprising:
   a) a tray;
   b) separate sections, each section containing a substrate having a single recess and a lid covering the recess;
   c) an orthodontic article in each recess; and
   d) separate means cooperating with said tray, each means adapted to carry one of said sections and permit individual removal and replacement of said carried section.

2. The assembly of claim 1 wherein the orthodontic article is an orthodontic bracket.

3. The assembly of claim 2 wherein the orthodontic bracket has a light-curable paste thereon.

4. The assembly of claim 1 wherein the lid is opaque to actinic radiation.

5. The assembly of claim 4 wherein the lid is resealable.

6. The assembly of claim 4 wherein the orthodontic article is an orthodontic bracket having a light-curable paste thereon.

7. The assembly of claim 1 wherein the orthodontic article is a light-curable paste.

8. The assembly of claim 1 wherein the lid is resealable.

9. The assembly of claim 1 wherein the tray includes a cover.

10. The assembly of claim 1 wherein the means comprises holes in the tray, each hole receiving one of the substrates.

11. The assembly of claim 10 wherein the orthodontic article is an orthodontic bracket.

12. The assembly of claim 11 wherein the orthodontic bracket has a light-curable paste thereon.

13. The assembly of claim 10 wherein the lid is opaque to actinic radiation.

14. The assembly of claim 13 wherein the lid is resealable.

15. The assembly of claim 13 wherein the orthodontic article is an orthodontic bracket having a light-curable paste thereon.

16. The assembly of claim 13 wherein the orthodontic article is a light-curable paste.

17. The assembly of claim 10 wherein the lid is resealable.

18. The assembly of claim 10 wherein the tray includes a cover.

* * * * *

UNITED STATES PATENT AND TRADEMARK OFFICE
CERTIFICATE OF CORRECTION

PATENT NO. : 5,762,192
DATED : June 9, 1998
INVENTOR(S) : Dwight W. JACOBS, Kenneth E. HOEVEL and
Bruce E. CHESTER It is certified that error appears in the above-indentified patent and that said Letters Patent is hereby corrected as shown below:

On the cover page of the patent, item "[*]", line 3, delete "5,978,007", and insert therefor --4,978,007, 5,636,736, or 5,348,154--.

Signed and Sealed this

Eighth Day of December, 1998

Attest:

BRUCE LEHMAN

Attesting Officer

Commissioner of Patents and Trademarks